(12) United States Patent
Love

(10) Patent No.: US 6,425,902 B1
(45) Date of Patent: Jul. 30, 2002

(54) SURGICAL INSTRUMENT FOR HEART VALVE RECONSTRUCTION

(75) Inventor: Jack W. Love, Santa Barbara, CA (US)

(73) Assignee: CardioMend LLC, Santa Barbara, CA (US)

( * ) Notice: Subject to any disclaimer, the term of this patent is extended or adjusted under 35 U.S.C. 154(b) by 0 days.

(21) Appl. No.: 09/849,762

(22) Filed: May 4, 2001

(51) Int. Cl.[7] .................................................. A61B 17/04

(52) U.S. Cl. ...................................... 606/150; 623/2.11

(58) Field of Search ................................. 606/139, 144, 606/150, 151, 153; 623/2.1, 2.11, 2.12, 2.15, 2.2, 2.38, 2.13, 2.19

(56) References Cited

U.S. PATENT DOCUMENTS

| | | | |
|---|---|---|---|
| 3,320,972 A | 5/1967 | High et al. ............... 137/525.1 |
| 3,655,306 A | 4/1972 | Ross et al. ................... 425/109 |
| 4,470,157 A | 9/1984 | Love ............................... 3/1.5 |
| 4,731,075 A | 3/1988 | Gallo Mezo et al. ........... 623/2 |
| 4,960,424 A | 10/1990 | Grooters ........................ 623/2 |
| 5,147,391 A | 9/1992 | Lane .............................. 623/2 |
| 5,156,621 A | 10/1992 | Navia et al. .................... 623/2 |
| 5,163,955 A | 11/1992 | Love et al. ..................... 623/2 |
| 5,197,979 A | 3/1993 | Quintero et al. ............... 623/2 |
| 5,258,021 A | 11/1993 | Duran ............................ 623/2 |
| 5,297,564 A | 3/1994 | Love ........................... 128/898 |
| 5,326,370 A | 7/1994 | Love et al. ..................... 623/2 |
| 5,326,371 A | 7/1994 | Love et al. ..................... 623/2 |
| 5,336,258 A | 8/1994 | Quintero et al. ............... 623/2 |
| 5,344,442 A | 9/1994 | Deac .............................. 623/2 |
| 5,352,240 A | 10/1994 | Ross .............................. 623/2 |
| 5,370,685 A | 12/1994 | Stevens ......................... 623/2 |
| 5,376,112 A | 12/1994 | Duran ............................ 623/2 |
| 5,411,552 A | 5/1995 | Andersen et al. .............. 623/2 |
| 5,423,887 A | 6/1995 | Love et al. ..................... 623/2 |
| 5,425,741 A | 6/1995 | Lemp et al. ................. 606/167 |
| 5,449,384 A | 9/1995 | Johnson ........................ 623/2 |
| 5,480,424 A | 1/1996 | Cox ............................... 623/2 |
| 5,489,296 A | 2/1996 | Love et al. ..................... 623/2 |

(List continued on next page.)

FOREIGN PATENT DOCUMENTS

| | | |
|---|---|---|
| EP | 0 581 233 | 2/1994 |
| FR | 2 399 832 | 9/1979 |
| WO | WO92/03990 | 3/1992 |
| WO | WO92/12690 | 8/1992 |
| WO | WO92/13502 | 8/1992 |
| WO | WO93/18721 | 9/1993 |
| WO | WO95/16411 | 6/1995 |

OTHER PUBLICATIONS

Aug. 20, 1993 P. Zioupos and J.C. Barbenel Mechanics of native bovine pericardium. I. The multiangular behavior of strength and stiffness of the tissue. Biomaterials 1994, vol. 15, pp. 366–373.

(List continued on next page.)

Primary Examiner—Danny Worrell
(74) Attorney, Agent, or Firm—Bryan Cave LLP

(57) ABSTRACT

A surgical instrument for holding a piece of tissue in a configuration of an open circulatory system valve to facilitate surgical attachment of the tissue to the patient's valve annulus. The instrument includes an inner member having a handle portion at one end and an inner tissue holding portion at the opposite end. The inner tissue holding portion includes one or more of inner leaves. An outer member disposed about the inner member includes an outer tissue holding portion having one or more of outer leaves that are complementary and can be engaged with the inner leaves. A collet or other actuator moves the outer leaves radially inward and outward with respect to the inner leaves. The outer leaves are separated from the inner leaves to allow placement of the tissue on the inner leaves. The outer leaves are then moved radially inward to hold the tissue between the leaves in a configuration of one or more leaflets of an open circulatory system valve to facilitate surgical attachment.

15 Claims, 12 Drawing Sheets

U.S. PATENT DOCUMENTS

| | | | |
|---|---|---|---|
| 5,489,298 A | | 2/1996 | Love et al. ..................... 623/2 |
| 5,503,638 A | | 4/1996 | Cooper et al. ................. 623/11 |
| 5,509,930 A | | 4/1996 | Love .............................. 623/2 |
| 5,522,885 A | * | 6/1996 | Love et al. .............. 137/515.7 |
| 5,531,784 A | | 7/1996 | Love et al. ..................... 623/2 |
| 5,531,785 A | | 7/1996 | Love et al. ..................... 623/2 |
| 5,571,174 A | | 11/1996 | Love et al. ..................... 623/2 |
| 5,584,878 A | | 12/1996 | Love et al. ..................... 623/2 |
| 5,662,705 A | | 9/1997 | Love et al. ..................... 623/2 |
| 5,716,399 A | | 2/1998 | Love .............................. 623/2 |
| 5,755,782 A | | 5/1998 | Love et al. ..................... 623/2 |
| 5,800,531 A | * | 9/1998 | Cosgrove et al. .......... 623/2.11 |
| 5,957,976 A | * | 9/1999 | Vanney et al. ................. 623/2 |
| 6,019,790 A | * | 2/2000 | Holmberg et al. ............ 606/99 |
| 6,129,758 A | | 10/2000 | Love ......................... 623/2.11 |
| 6,197,053 B1 | * | 3/2001 | Cosgrove et al. .......... 623/2.11 |
| 6,283,993 B1 | * | 9/2001 | Cosgrove et al. .......... 623/2.11 |
| 6,328,763 B1 | * | 12/2001 | Love et al. ................ 623/2.13 |

OTHER PUBLICATIONS

1994 P. Zioupos, J.C. Barbenel, J. Fisher Anisotropic elasticity and strength of glutaraldehyde fixed bovine pericardium for use in pericardial bioprosthetic valves, Journal of Biomedical Materials Research, vol. 28, 49–57 (1994).

1993 P. Zioupos, J.C. Barbenel, J. Fisher, D.C. Wheatley Changes in mechanical properties of bioprosthetic valve leaflets made of bovine pericardium, as a result of long–term mechanical conditioning in vitro and implantation in vivo, Journal of Materials Science: Materials in Medicine, 531–537, 1993.

1974 W. Milton Swanson, Richard E. Clark Dimensions and Geometric Relationships of the Human Aortic Valve as a Function of Pressure, Circulation Research, vol. 35 (1974).

1999 Steven Kahn Cedars–Sinai Medical Center Prosthetic Valve Information Page, Steven Kahn, M.D., Division of Cardiothoracic Surgery, Cedars–Sinai Medical Center.

Aug. 13, 2000 James G. Hanlon, Robert W. Suggitt, Jack W. Love Advances in Seminular Heart Valve Reconstruction, World Congress of International Society of Cardio–Thoracic Surgeons, Aug. 13–16, 2000.

* cited by examiner

SURGICAL INSTRUMENT FOR HEART VALVE RECONSTRUCTION

FIELD OF THE INVENTION

The present invention pertains to the field of heart valve repair and reconstruction. More particularly, this invention relates to a surgical instrument for holding tissue used in heart valve reconstruction.

BACKGROUND OF THE INVENTION

For nearly forty years, since the advent of the heart-lung machine, it has been possible to repair and reconstruct diseased heart valves. The concept of repairing, rather than replacing, diseased heart valves began with the work of Professor Ake Senning of Zurich in 1960. (Senning A.: Fascia Lata Replacement of Aortic Valves. *Journal Thoracic and Cardiovascular Surgery* 54: 465–70 (1967).) However, until recently, methods for reconstructing semilunar valves have generally been characterized by lack of precision and reproducibility.

To overcome these and other disadvantages of the prior methods of valve reconstruction, the inventor of the subject invention developed improved, more easily reproducible, less complicated, and generally standardized, methods of reconstructing heart valves. These methods are generally described in Love U.S. Pat. No. 5,716,399 and Love U.S. Pat. No. 6,129,758, and copending U.S. Application Ser. No. 09/330, 689 of Love, et al. (collectively referred to as the "Love Patents"), each of which is incorporated herein by reference in its entirety. The Love Patents generally describe methods for repairing or reconstructing heart valves preferably using a novel unitary trefoil tissue pattern. An embodiment of these methods can preferably include the steps of (a) sizing of the heart valve based on the distance between adjacent commissures of the native valve annulus; (b) cutting a trefoil tissue pattern corresponding in size to the native valve annulus; (c) temporarily mounting the tissue pattern on a surgical instrument for holding the tissue in a configuration of a heart valve to facilitate attachment of the tissue; and (d) suturing the tissue to the native valve annulus.

The Love Patents disclose an innovative surgical instrument for holding the tissue pattern in a configuration of at least one leaflet of a circulatory system valve. An embodiment of the device described therein is shown in prior art FIG. 1. The instrument generally comprises an upper former 11 having a handle 12, and a lower former 13 having a handle 14. The tissue pattern 15 is placed between upper former 11 and the lower former 13. The formers are brought into complementary engagement by inserting handle 14 into handle 12 and sliding the upper former 11 against the lower former 13. The tissue pattern 15 is held in the configuration of the a closed or partially closed circulatory system valve to allow the tissue pattern 15 to be surgically attached to the native valve annulus.

The present invention relates to a novel variation of a surgical instrument for holding a piece of tissue in a configuration of a circulatory system valve, which provides a number of desirable features not present in the device described in the Love Patents or any other prior devices. The instrument disclosed herein allows the tissue to be surgically attached in an open valve configuration (rather than in the closed or partially closed configuration required by prior devices). The present invention also avoids rubbing of the two tissue forming surfaces so as to reduce the risk of slippage or damage to the tissue when engaging the tissue forming surfaces. In addition, the tissue holding instrument disclosed herein can be manufactured at relatively low cost because it has few parts, which can be manufactured of low-cost plastic materials. The claimed invention provides a new, useful and unique surgical instrument for holding a piece of tissue in a configuration of one or more leaflets of an open circulatory system valve, which provides these and other advantageous features.

SUMMARY OF THE INVENTION

The present invention relates to a surgical instrument for holding a piece of tissue in a configuration of at least one leaflet of an open circulatory system valve to facilitate surgical attachment of the tissue. The instrument includes an inner member having a proximal end comprising a handle portion and a distal end comprising an inner tissue holding portion. The inner tissue holding portion has of one or more inner leaves. An outer member is disposed about the inner member. The outer member has an outer tissue holding portion comprising one or more of outer leaves. The inner and outer leaves preferably correspond to the shape of leaflets of a circulatory system valve and may be brought together into complementary engagement with a piece of tissue held between the inner and outer leaves. An actuator, such as a collet, moves the outer leaves radially inward and outward with respect to the inner leaves. The outer leaves are separated from the inner leaves to allow placement of the tissue on the inner leaves. The outer leaves are moved radially inward to hold the tissue between the leaves in a configuration of at least one leaflet of an open circulatory system valve to facilitate surgical attachment to the native valve annulus.

The outer member preferably includes a sleeve slidably disposed about the inner member and one or more arms connecting the outer leaves to the sleeve. The outer member is slid axially toward the proximal end of the inner member to facilitate placement of the tissue on the inner leaves and slid axially toward the distal end to engage the inner and outer leaves.

Each arm is preferably positioned within a groove on the collet that cooperates with the arm to actuate movement of the outer leaves when the collet is slid axially along the arms.

The instrument also preferably includes a tissue loading member. One end of the tissue loading member is engaged with the distal end of the inner member. The other end of the tissue loading member includes a rounded portion for facilitating the placement of the tissue on the inner leaves.

The instrument also preferably includes a locking mechanism for retaining the actuator in place to keep the inner and outer leaves pressed together in complementary engagement, and to prevent linear movement and rotation of the outer member relative to the inner member.

The instrument is preferably provided in a kit comprising a plurality of instruments. Each instrument is one of a predetermined range of sizes corresponding to a range of anatomical sizes of normal human heart valves.

DRAWINGS

These, and other features, aspects and advantages of the present invention will become more fully apparent from the following detailed description, appended claims, and accompanying drawings where:

DETAILED DESCRIPTION OF THE INVENTION

The subject invention provides a new, useful and unique surgical instrument for holding a piece of tissue in a configuration of one or more leaflets of an open circulatory system valve to facilitate surgical attachment of the tissue. The instrument is particularly suited for reconstruction of cardiac semilunar valves (aortic and pulmonic) utilizing the methods described in Love U.S. Pat. No. 5,716,399 (incorporated herein by reference in its entirety).

Figure 2:
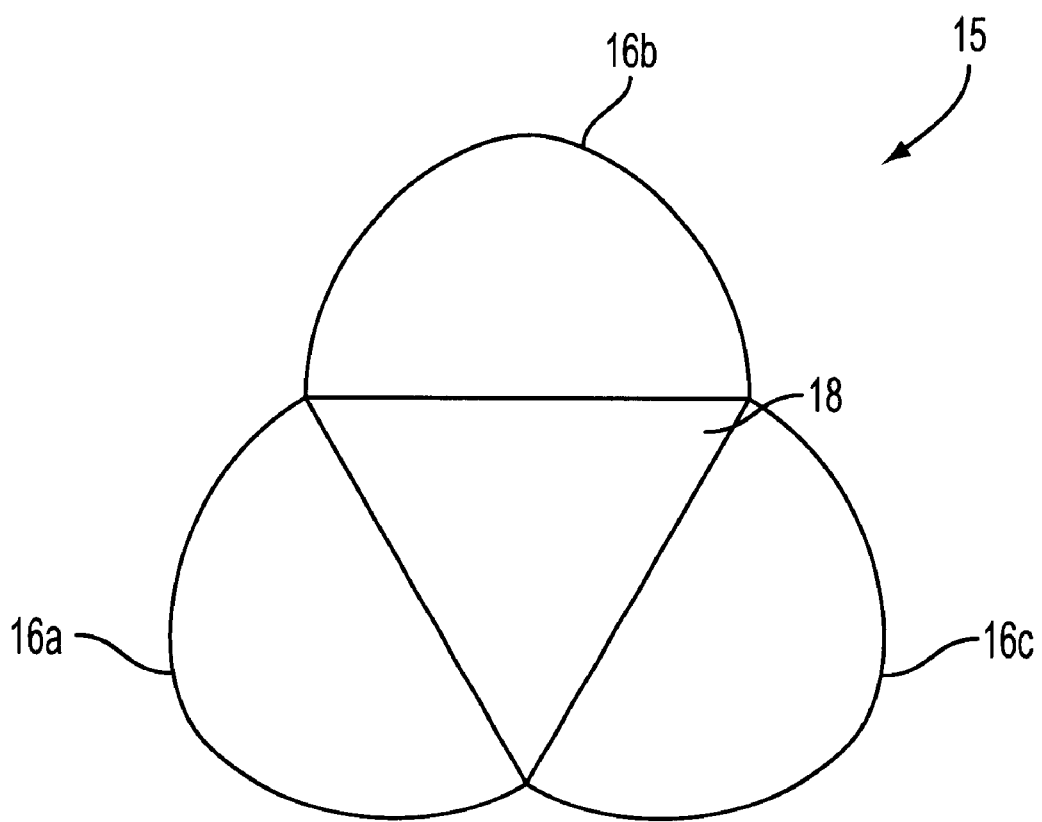
FIG. 2 is a front view of a preferred trefoil tissue pattern for use with the subject invention.
Figure 3:
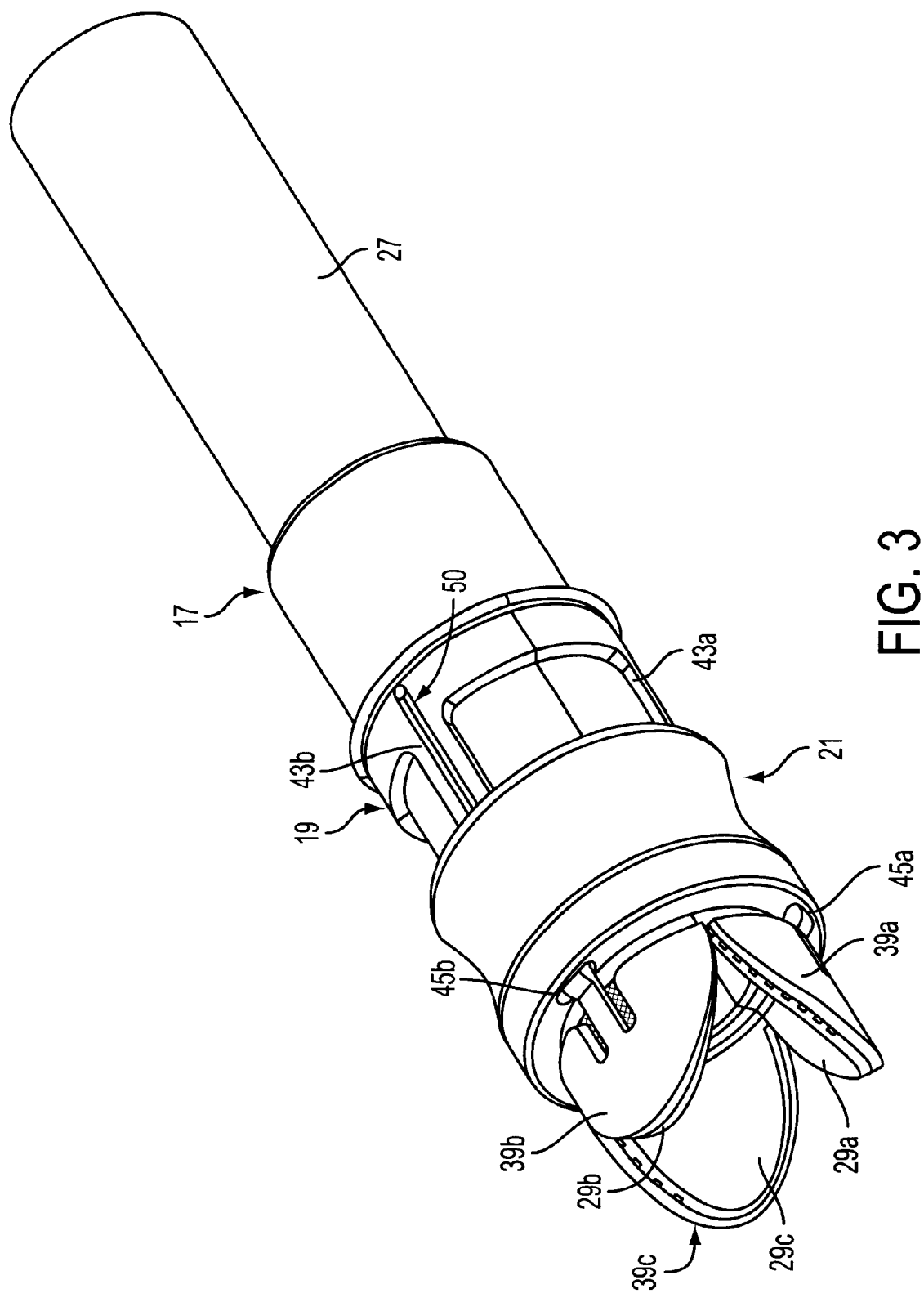
FIG. 3 is a perspective view of an embodiment of the surgical instrument of the subject invention in an engaged/closed position.
Figure 4:
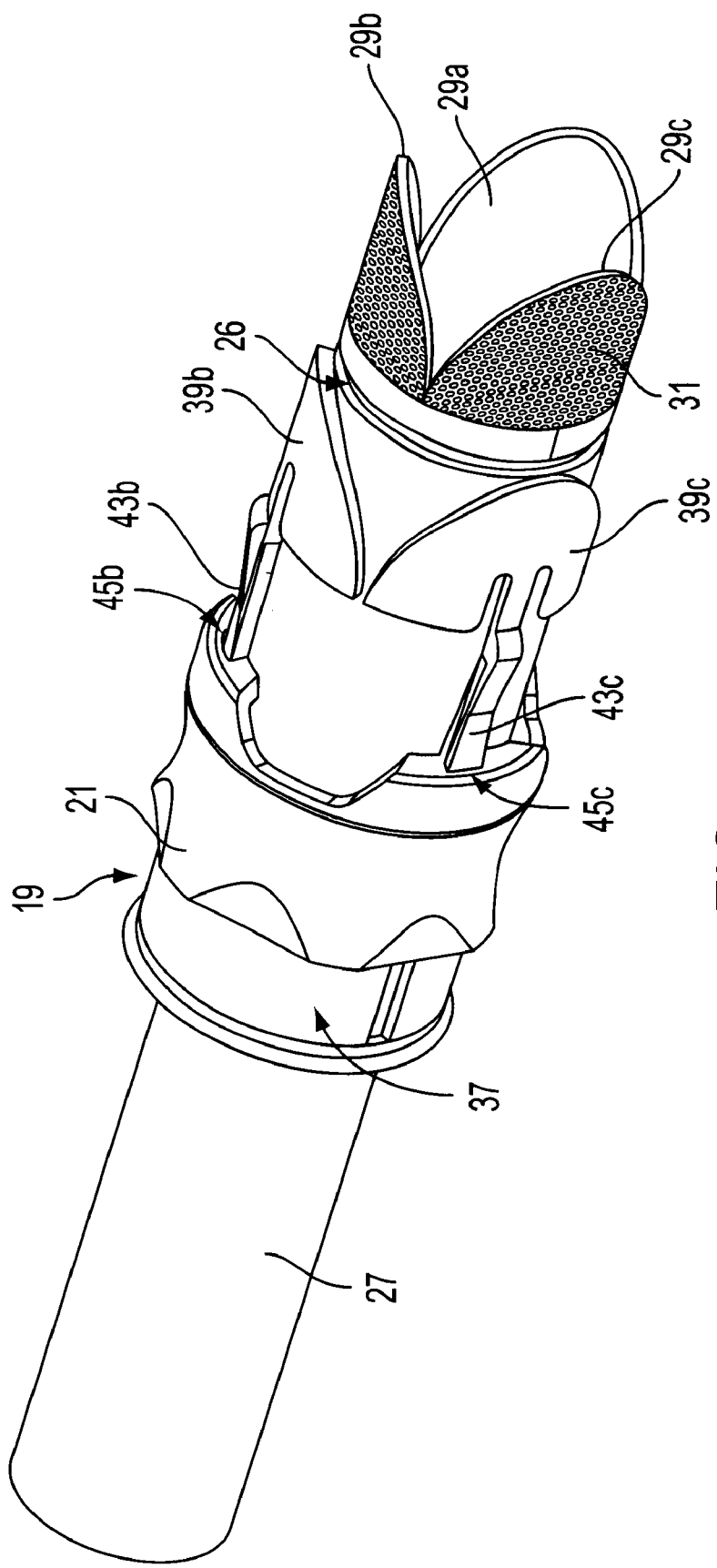
FIG. 4 is a perspective view of an embodiment of a surgical instrument of the subject invention showing the leaves in a disengaged/open position.
Figure 5:
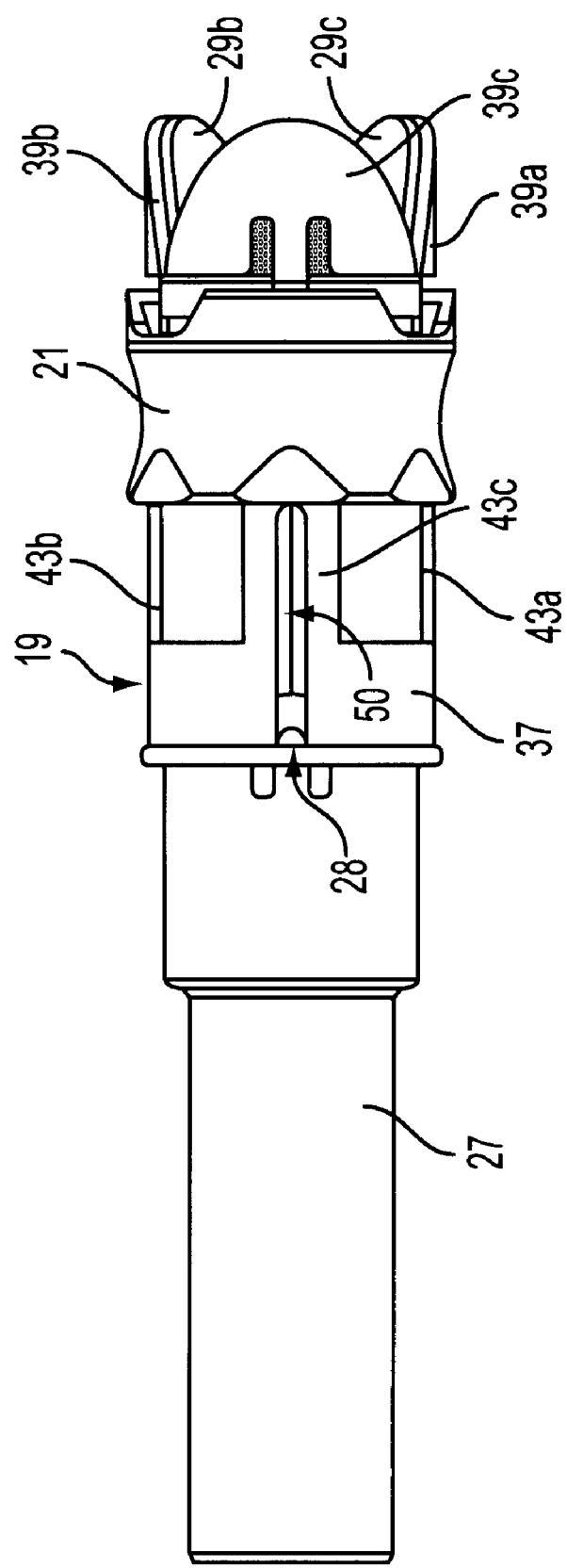
FIG. 5 is a side view of an embodiment of a surgical instrument of the subject invention showing the leaves in an engaged/closed position.
Figure 6:
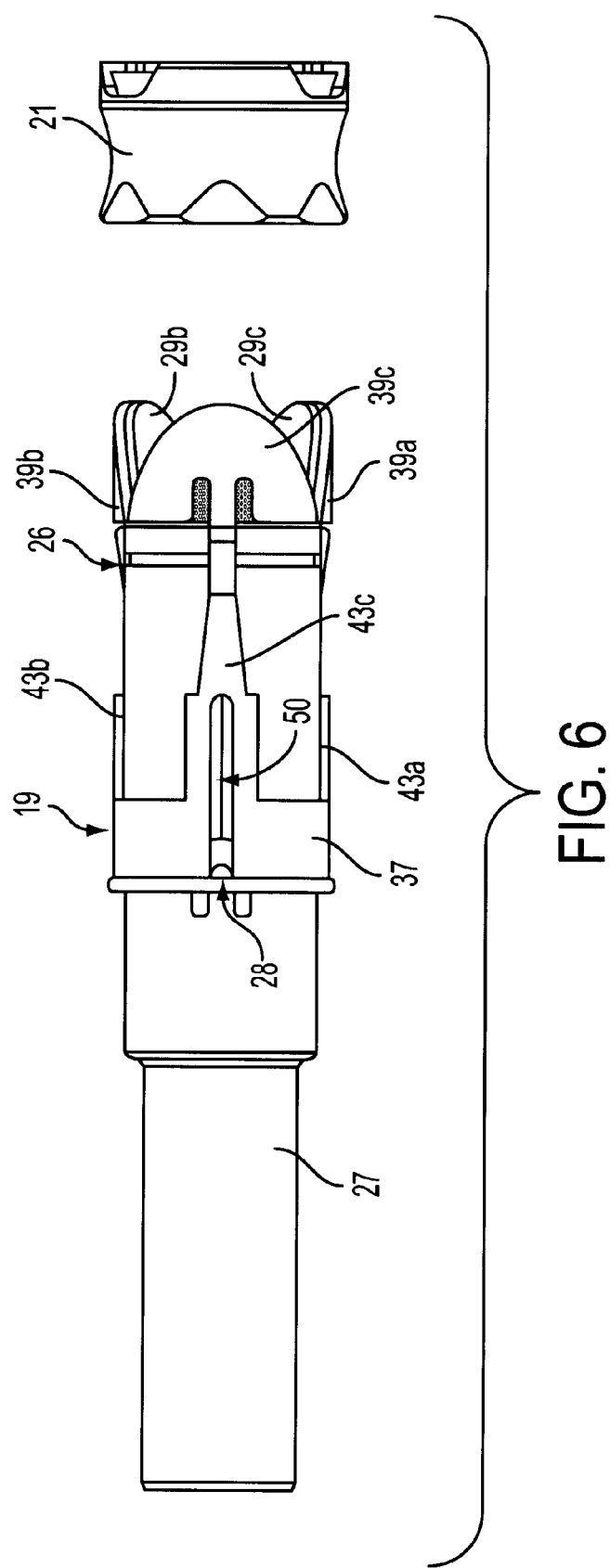
FIG. 6 is a side view of an embodiment of a surgical instrument of the subject invention with the collet removed.

FIG. 2 illustrates a preferred tissue pattern for use with the subject invention. The tissue pattern is fully described and shown in copending U.S. app. Ser. No. 09/330,689 (incorporated herein by reference in its entirety). The trefoil pattern is used to form the preferred tri-leaflet valve structure. An embodiment of the trefoil valve tissue pattern 15 has three lobes, 16a, 16b and 16c, arranged about a center orifice 18. Each of lobes 16a, 16b and 16c of the trefoil valve tissue pattern, when oriented in the configuration of a valve and affixed to the native valve annulus, will form one leaflet or lobe of the valve structure. The tissue pattern is preferably cut in a predetermined size that corresponds to the size of the native valve annulus.

FIGS. 3–12 illustrate an embodiment of a surgical instrument for holding a piece of tissue in a configuration of at least one leaflet of a circulatory system valve to facilitate surgical attachment of the tissue. As shown in FIGS. 3–6, the instrument preferably comprises three principal components: inner member 17, outer member 19, and collet 21.

Figure 7:
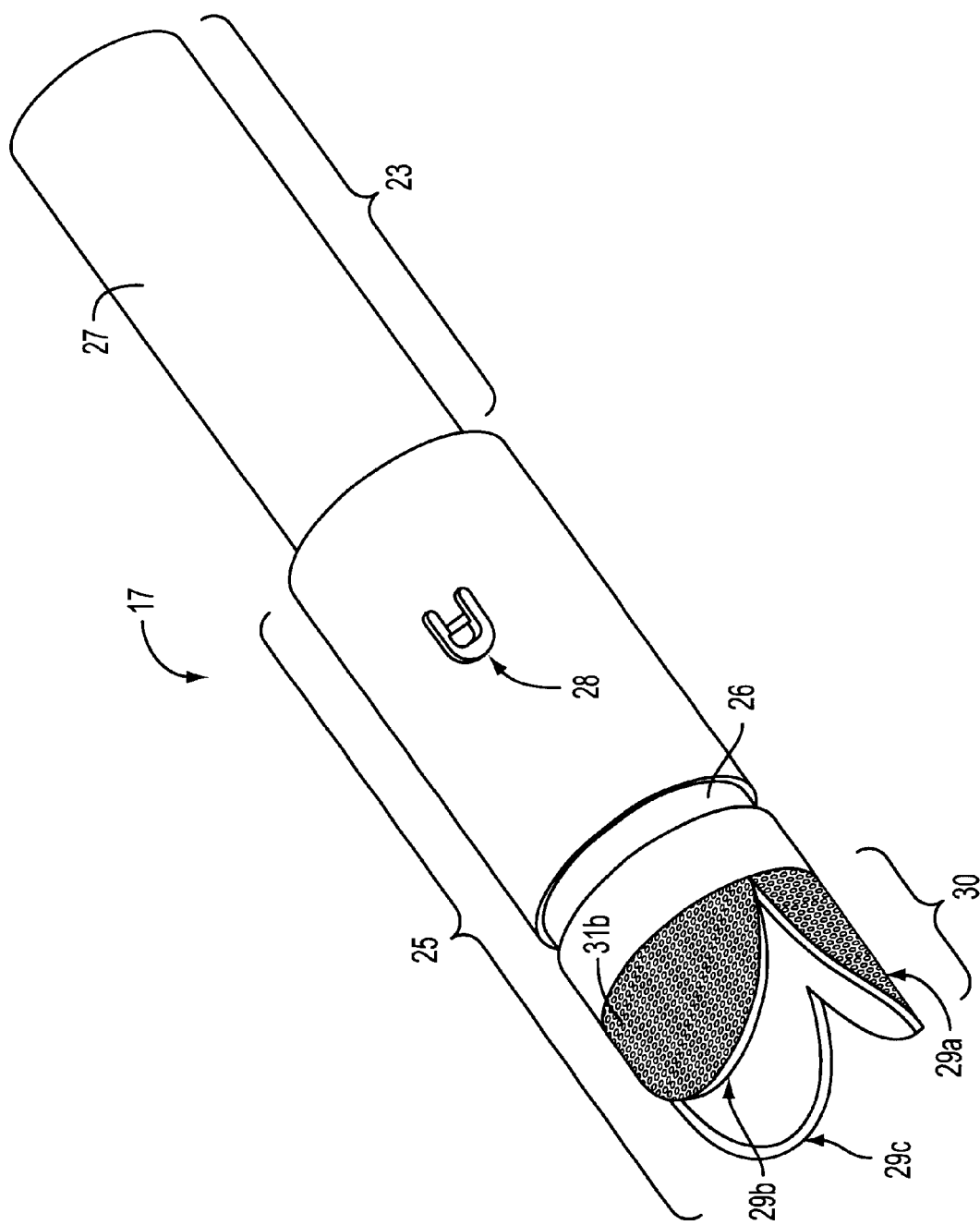
FIG. 7 is a perspective view of the inner member of an embodiment of the subject invention.

FIG. 7 shows an example of inner member 17 of an embodiment of the instrument. Inner member 17 is preferably cylindrical to conform to the shape of the native valve annulus; however, those skilled in the art will appreciate that various other shapes are possible. Inner member 17 has a proximal end 23 and a distal end 25. At the proximal end 23, inner member 17 includes a handle 27. Handle 27 preferably has a circumference that is slightly smaller than the circumference at the distal end 25 of the inner member 17 to provide a comfortable holding area. Inner member 17 has a tissue holding portion 30 (referred to as an inner tissue holding portion) three leaves 29a, 29b and 29c (referred to as inner leaves). The leaves are preferably in a shape that conforms to the shape of the leaflets of an open tri-leaflet circulatory system valve. Each of the three inner leaves 29a, 29b and 29c preferably includes a tissue retention region 31, which uses friction to facilitate retention of the tissue on the leaf. The tissue retention region may comprise any of a number of means for retaining the tissue on the leaf, which preferably avoids trauma to the tissue. For example the tissue retention region may comprise a region of dimples, texturing, holes, ridges, pebbling, etches, or grooves to provide a surface to facilitate holding of th[0085] tissue.

Figure 8:
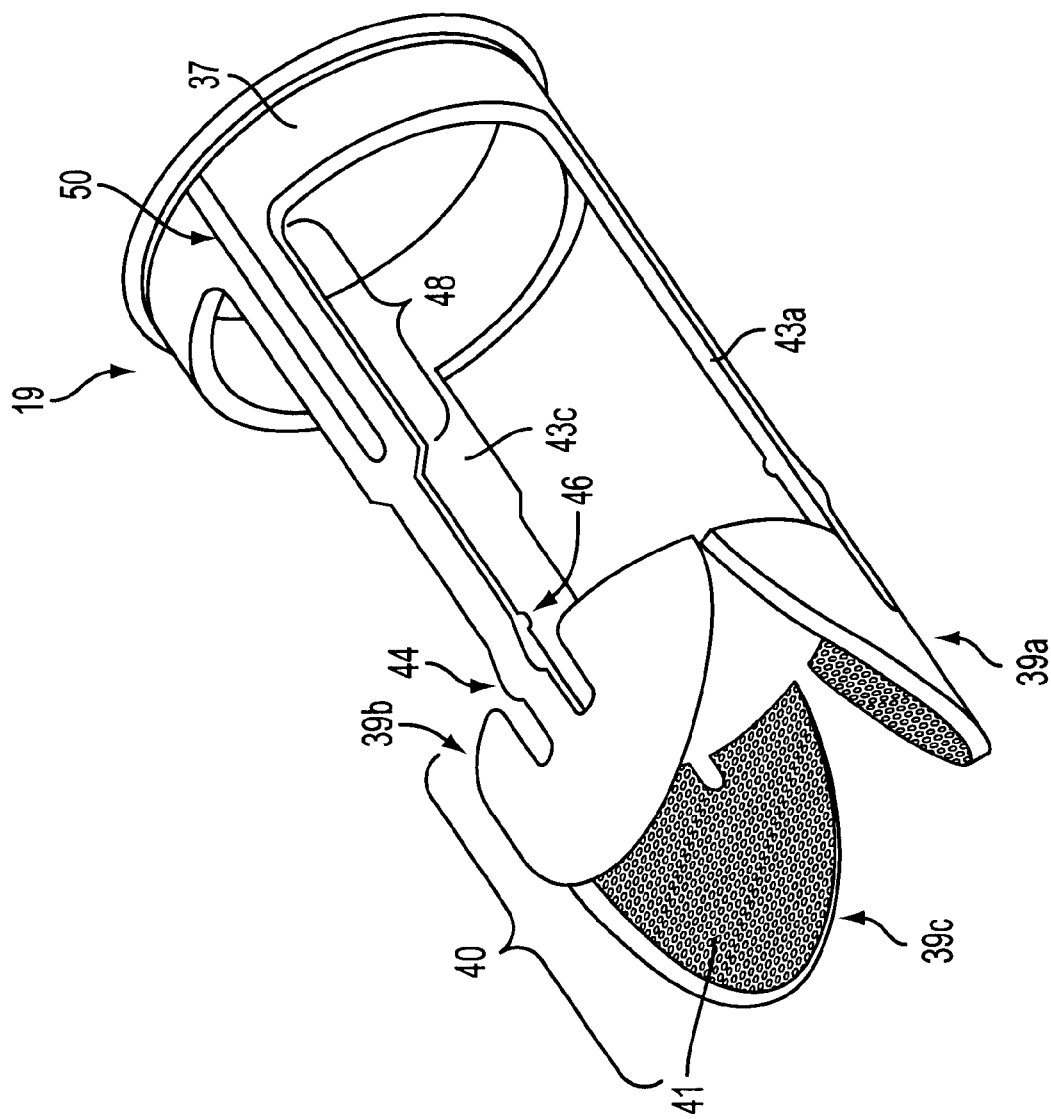
FIG. 8 is a perspective view of the outer member of an embodiment of the subject invention.

FIG. 8 is a perspective view of the outer member 19 of an embodiment of the instrument. Outer member 19 comprises sleeve 37, which slides over the distal end 25 of the inner member 17. In one embodiment, sleeve 37 is a cylindrical portion that slides over a cylindrical inner member 17. Sleeve 37 need not necessarily be cylindrical, but preferably conforms to the shape of inner member 17 so that it can be slid over inner member 17. Outer member 19 includes a tissue holding portion 40 (referred to as an outer tissue holding portion), which comprises three leaves 39a, 39b and 39c (referred to a outer leaves). Outer leaves 39a, 39b and 39c preferably conform to the shape of the leaflets of an open circulatory system valve. The outer leaves 39a, 39b and 39c are complementary and engageable with the inner leaves 29a, 29b and 29c (e.g., a convex outer surface of the inner leaf mates with a concave inner surface of the outer leaf). The outer leaves 39a, 39b and 39c and the inner leaves 29a, 29b and 29c need not be completely complementary but should possess sufficient complementarity to provide the functions and results disclosed herein. The inner leaves 29a, 29b, 29c and outer leaves 39a, 39b, 39c are engaged (i.e., brought together in complementary engagement) while the trefoil pattern of tissue is sandwiched between the inner and outer leaves to form the tri-leaflet valve repair structure. Outer leaves 39a, 39b and 39c may also include a tissue retention region 41 (e.g., dimples, texturing, holes, ridges, pebbling, etches, or grooves to facilitate holding of the tissue) which uses friction to facilitate retention of the tissue on the leaf. Outer member 19 preferably further comprises arms 43a, 43b and 43c between leaves 39a, 39b and 39c and sleeve 37. In the embodiment shown, arms 43a, 43b and 43c are tapered outward toward sleeve 37 to facilitate radial movement of the outer leaves when engaged with collet 21 as discussed below.

Figure 9A:
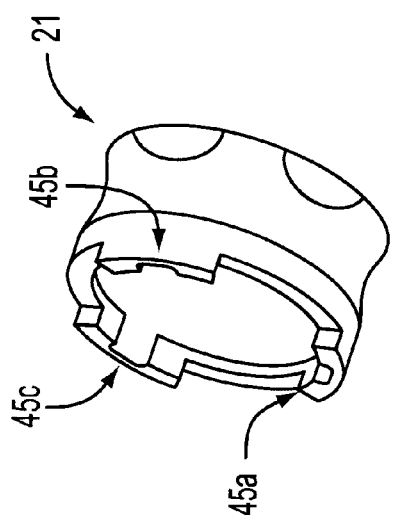
FIG. 9A is a perspective view of the collet of an embodiment of the instrument of the subject invention.
Figure 9B:
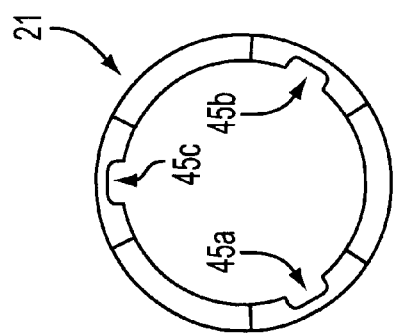
FIG. 9B is a top view of the collet of an embodiment of the instrument of the subject invention.

FIGS. 9A and 9B illustrate the collet 21 of an embodiment of the instrument. The term collet broadly refers to any device disposed about the outer member 19 for actuating movement of the outer leaves 39a, 39b and 39c radially inward and outward with respect to the stationary inner leaves 29a, 29b, 29c. In the embodiment shown, collet 21 is a ring-shaped member that that fits over outer member 19. Collet 21 preferably comprises grooves 45a, 45b and 45c to facilitate movement of arms 43a, 43b and 43c. As shown in FIGS. 3–6, arms 43a, 43b and 43c fit within grooves 45a, 45b and 45c of collet 21 and are engaged therewith to produce radial movement of outer leaves 39a, 39b and 39c. Collet 21 may be slid axially (i.e., back and forth between proximal and distal ends) along arms 43a, 43b and 43c. As collet 21 is slid along tapered arms 43a, 43b and 43c, grooves 45a, 45b and 45c cooperate with arms 43a, 43b and 43c to cause outer leaves 39a, 39b and 39c to move radially outward and inward with respect to inner 20 member 17. As collet 21 is moved toward sleeve 37, outer leaves 39a, 39b and 39c move radially outward with respect to inner member 17. As collet 21 is moved toward the outer leaves 39a, 39b and 39c, outer leaves 39a, 39b and 39c move radially inward with respect to inner member 17 to bring outer leaves 39a, 39b and 39c into complementary engagement with inner leaves 29a, 29b and 29c. As those skilled in the art will appreciate, there are numerous other mechanisms that could be employed to actuate radial movement of outer leaves 39a, 39b and 39c. The term actuator is used herein to broadly refer to collet 21 and any of various alternative mechanisms for actuating movement of the outer leaves 39a, 39b and 39c radially inward and outward with respect to the stationary inner leaves 29a, 29b, 29c.

Figure 1:
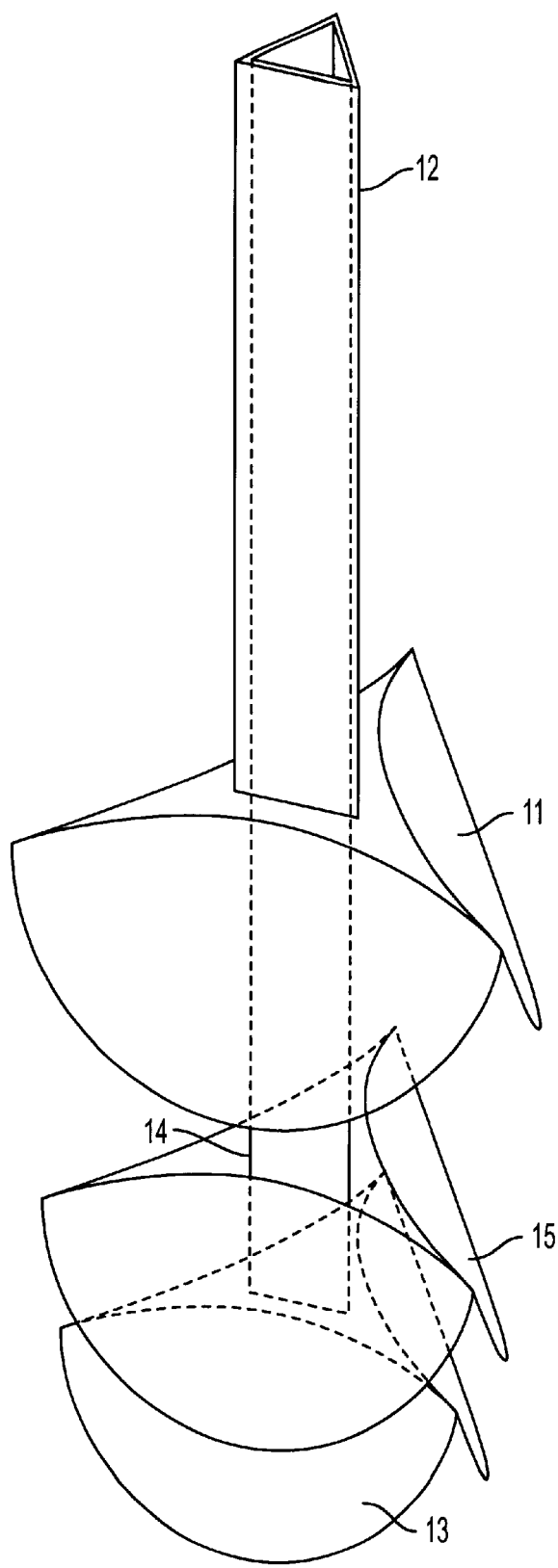
FIG. 1 is a partially exploded perspective view of a prior art instrument for holding a piece of tissue in a configuration of a circulatory system valve.

In contrast to prior devices such as the device illustrated in FIG. 1, the outer leaves 39a, 39b and 39c of the instrument described herein move radially inward and outward with no lateral sliding against the tissue surface. This radial movement provides a number of significant advantages. For example, the radial movement of the leaves avoids the possibility of pushing the tissue off of the forming surfaces when engaging the leaves. The radial movement also avoids the risk of damaging the tissue as a result of sliding action between the forming surfaces.

Each of arms 43a, 43b and 43c preferably further includes an outer ridge 44 and an inner ridge 46. Outer ridge 44 cooperates with collet 21 to limit the axial sliding of collet 21 along arms 43a, 43b and 43c and to lock collet 21 in place to maintain inner leaves 29a, 29b and 29c in complementary engagement with outer leaves 39a, 39b and 39c. Inner ridge 46 cooperates with groove 26 on inner member 17 to prevent the axial movement of outer leaves 39a, 39b and 39c as collet 21 is slid along arms 43a, 43b and 43c away from the outer leaves 39a, 39b and 39c. Each of arms 43a, 43b and 43c also preferably includes a widened proximal portion 48 that is wider than the opening of grooves 45a, 45b and 45c on collet 21 so as to limit the axial sliding of collet 21 along arms 43a, 43b and 43c in the direction of sleeve 37. One of arms 43a, 43b and 43c also preferably includes a travel limit slot 50 that cooperates with a travel limit stop 52 on inner member 17 to limit the axial sliding of outer member 19 and along inner member 17 and to prevent the rotation of outer member 19 about inner member 17. Those skilled in the art will appreciate that there are numerous other alternative mechanisms that could be employed to maintain inner leaves 29a, 29b and 29c in complementary engagement with outer leaves 39a, 39b and 39c, and to limit the axial and rotational movement of collet 21 and outer member 19.

Figure 10:
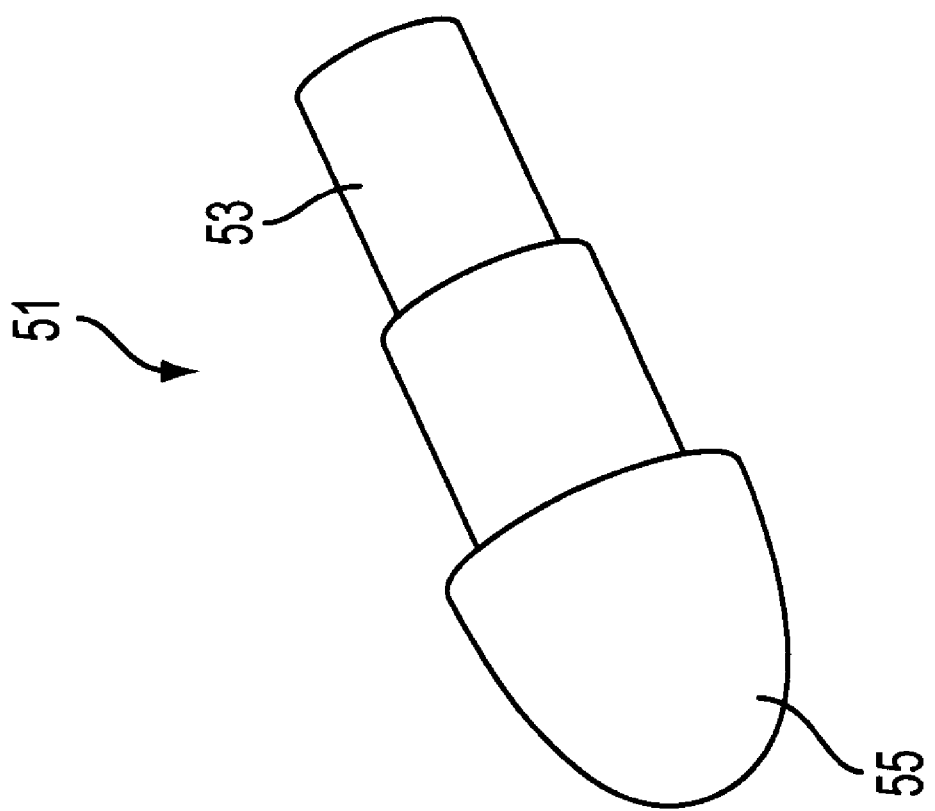
FIG. 10 is a perspective view of the tissue loading member of an embodiment of the instrument of the subject invention.
Figure 11:
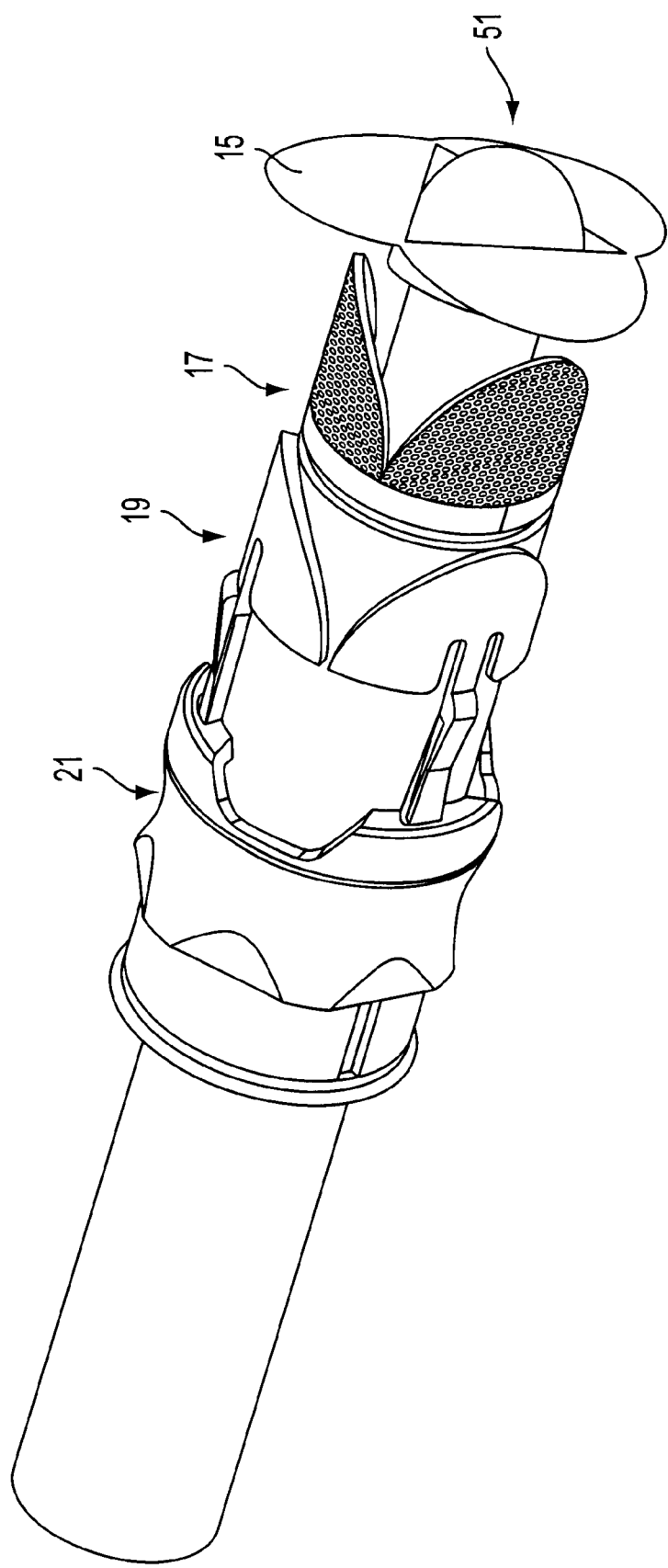
FIG. 11 is a perspective view of the tissue loading member being used to load tissue on the instrument.

FIG. 10 illustrates a tissue loading member 51 of an embodiment of the instrument of the present invention. The tissue loading member 51 has a proximal end 53 and a distal end 55. The proximal end 53 of the tissue loading member 51 is preferably a cylindrical portion that is sized to be inserted into the distal end 25 of the inner member 17. The distal end 55 of the tissue loading member 51 is preferably a rounded (e.g., ellipsoidal) portion for facilitating the placement of the tissue 15 on the inner leaves 29a, 29b and 29c as is illustrated in FIG. 11. After loading of the tissue on the inner leaves 29a, 29b and 29c, the tissue loading member 51 is preferably removed from the inner member 17.

Figure 12:
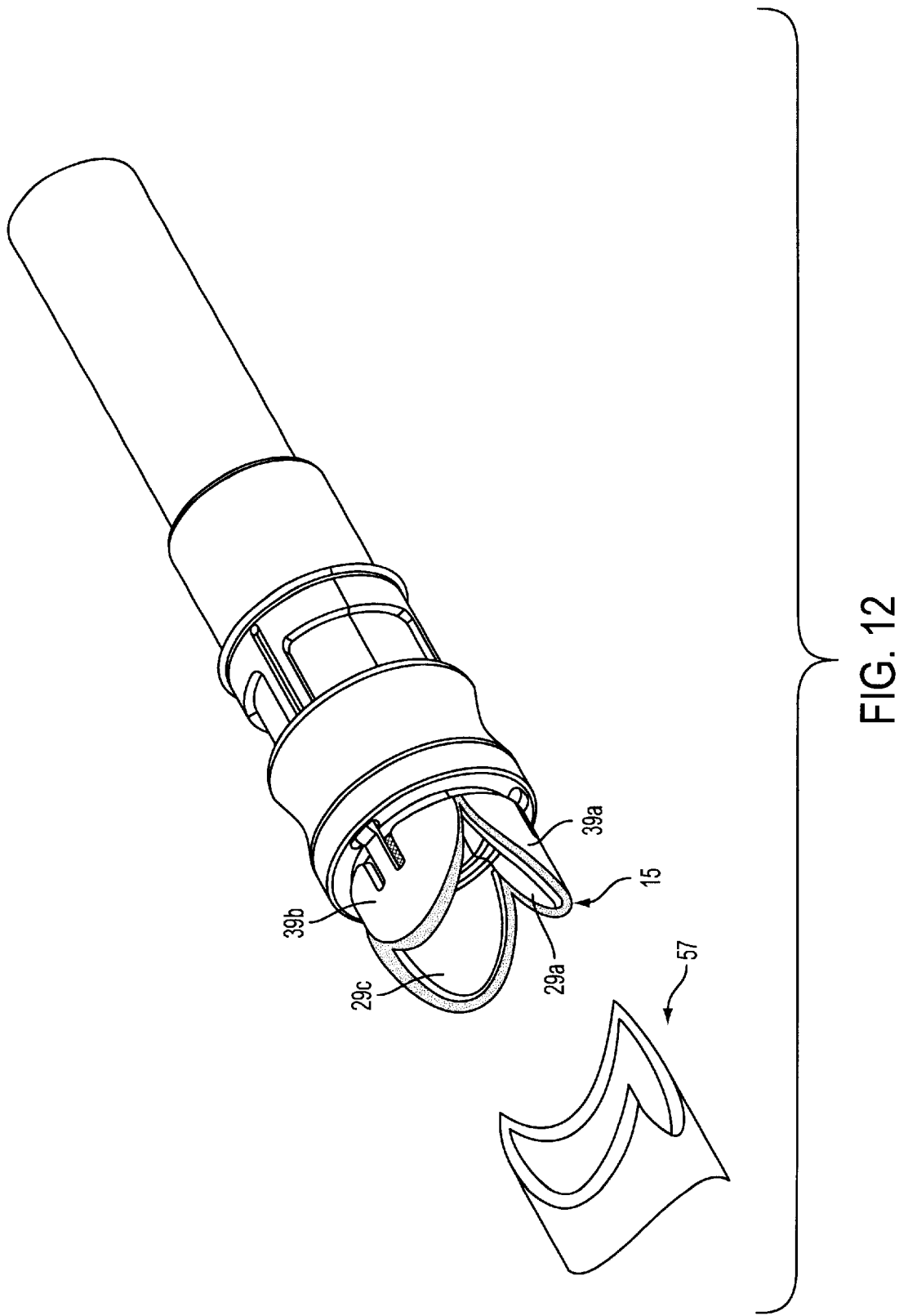
FIG. 12 is a perspective view of an embodiment of the instrument of the subject invention used to surgically attach tissue to a heart valve annulus.

As illustrated in FIG. 12, the tissue pattern is held between inner leaves 29a, 29b and 29c and outer leaves 39a, 39b and 39c in a configuration of at least one leaflet of an open circulatory system valve. A margin of tissue pattern 15 (preferably of approximately 3 mm) extending from the edge of the leaves is preferably surgically attached to the native valve annulus 57 with either continuous or interrupted sutures or by other suitable means. One of the many advantages of the device is that the margin of tissue pattern 15 extending from the edge of the leaves and the contour of the leaves can be used to guide placement of sutures or other means for surgically attaching the valve tissue to the native valve annulus 57. Another advantage of the present invention is that it allows the valve leaflets to be surgically attached in an open valve position. Prior devices, such as the instrument disclosed in FIG. 1, require that the valve be surgically attached in a closed or partially closed position.

The instrument is preferably molded, cast or machined, from a biocompatible thermoplastic material that can be readily sterilized and discarded after single use. All edges that contact tissue are round and smooth to avoid damage to the tissue. One of the many advantages of the instrument of the present invention is that it can be manufactured in four pieces (inner member 17, outer member 19, collet 21 and loading member 51) of low-cost biocompatible thermoplastic material materials with minimal assembly. Thus, this instrument can be manufactured at a relatively low cost as compared to prior devices. This feature of the present invention provides a significant advantage when used in connection with the methods of heart valve reconstruction described in the Love Patents. An initial step of the methods described therein involves sizing of the native heart valve annulus. The preferred tissue pattern is preferably cut size-specific to correspond to the native annulus size. The holding instrument of the present invention is also preferably sized to correspond to the native valve annulus/tissue pattern size. Accordingly, the holding instrument may be distributed in kits comprising a tissue pattern or cutting template that corresponds in size to the tissue holding instrument. Because the devices of the present invention can be constructed using a few low-cost plastic parts, it has the significant practical advantage of allowing the instrument to be produced in a range of sizes at relatively low cost.

Although the invention has been described with reference to specific embodiments, it will be understood by those skilled in the art that the examples are merely illustrative and various changes may be made without departing from the spirit or scope of the invention. For instance, the numerous details set forth herein relating to the configuration and use of the presently preferred embodiment of the instrument with the preferred trefoil tissue pattern, are provided to facilitate the understanding of the invention and are not provided to limit the scope of the invention. It should also be appreciated that the subject invention can be used to repair less than all, i.e., one or two leaflets of a discarded valve, using tissue patterns comprising one or two lobes. Accordingly, the disclosure of embodiments of the invention is intended to be illustrative of the scope of the invention and is not intended to be limiting. It is intended that the scope of the invention shall be limited only to the extent required by the appended claims.

I claim:

1. A surgical instrument for holding a piece of tissue in a configuration of at least one leaflet of an open circulatory system valve to facilitate surgical attachment of the tissue, the instrument comprising:
   a. an inner member having a proximal end comprising a handle portion and a distal end comprising an inner tissue holding portion, the inner tissue holding portion comprising one or more of inner leaves;
   b. an outer member disposed about the inner member, the outer member comprising an outer tissue holding portion, the outer tissue holding portion comprising one or more of outer leaves, wherein the outer leaves are complementary and engagable with the inner leaves; and c. an actuator for moving the outer leaves radially inward and outward with respect to the inner leaves, so that the outer leaves may be separated from the inner leaves to allow placement of the tissue on the inner leaves, and the outer leaves may be moved radially inward to hold the tissue between the leaves in a configuration of at least one leaflet of an open circulatory system valve.

2. The surgical instrument of claim 1, wherein the outer member further comprises a sleeve slidably disposed about the inner member and one or more arms connecting the outer leaves to the sleeve, so that the outer member may be slid axially toward the proximal end of the inner member to facilitate placement of the tissue on the inner leaves and slid axially toward the distal end to engage the inner and outer leaves.

3. The surgical instrument of claim 2, wherein the actuator comprises a collet disposed about the outer member.

4. The surgical instrument of claim 3, wherein sliding the collet axially along the arms of the outer member actuates radial movement of the outer leaves with respect to the inner leaves.

5. The surgical instrument of claim 4, wherein each arm is positioned within a groove on the collet that cooperates with the arm to actuate movement of the outer leaves when the collet is slid axially along the arms.

6. The surgical instrument of claim 1, wherein the inner member is substantially cylindrical.

7. The surgical instrument of claim 1, wherein the outer and inner leaves correspond to the shape of leaflets of a circulatory system valve.

8. The surgical instrument of claim 1, wherein the one or more leaves comprises three leaves.

9. The surgical instrument of claim 1, wherein the leaves have a tissue retention region comprising an area of dimples, texture, holes, ridges, pebbling, etches or grooves to facilitate holding of the tissue.

10. The surgical instrument of claim 1, further comprising a tissue loading member having a distal end and a proximal end, wherein the proximal end comprises a portion that is engagable with the distal end of the inner member, and wherein the distal end comprises a rounded portion for facilitating the placement of the tissue on the inner leaves.

11. The surgical instrument of claim 1, further comprising a locking mechanism for retaining the actuator in place to keep the inner and outer leaves pressed together in complementary engagement.

12. The surgical instrument of claim 1, further comprising a mechanism for limiting or preventing rotation of the outer member relative to the inner member.

13. The surgical instrument of claim 1, further comprising a mechanism for limiting axial movement of the outer member relative to the inner member.

14. The surgical instrument of claim 1, wherein the piece of tissue is precut in a preestablished geometrical pattern corresponding to the shape of at least one leaflet of a circulatory system valve.

15. A surgical instrument for holding a piece of tissue in a configuration of at least one leaflet of a circulatory system valve to facilitate surgical attachment of the tissue, wherein the tissue is precut in a preestablished geometrical pattern corresponding to the shape of at least one leaflet of a circulatory system valve, the instrument comprising:

a. a substantially cylindrical inner member having a proximal end comprising a handle portion and a distal end comprising an inner tissue holding portion, wherein the inner tissue holding portion comprises three inner leaves corresponding to the shape of leaflets of a circulatory system valve;

b. an outer member comprising a sleeve slidably disposed about the inner cylindrical member, an outer tissue holding portion, wherein the outer tissue holding portion comprises three outer leaves corresponding to the shape of leaflets of a circulatory system valve, and wherein the outer leaves are complementary and engagable with the inner leaves, and three arms connecting the outer leaves to the sleeve;

c. a collet disposed about the outer member for actuating movement of the outer leaves radially inward and outward with respect to the inner leaves, wherein each arm is positioned within a groove on the collet that cooperates with the arm to actuate movement of the outer leaves as the collet is slid axially along the arms, so that the outer leaves may be separated from the inner leaves to allow placement of the tissue on the outer leaves, and the outer leaves may be moved radially inward to hold the tissue between the leaves in a configuration of at least one leaflet of an open circulatory system valve;

d. a locking mechanism for retaining the collet in place to keep the inner and outer leaves pressed together in complementary engagement;

e. a mechanism for limiting or preventing the rotation of the outer member relative to the inner member; and f. a tissue loading member having a distal end and a proximal end, wherein the proximal end comprises a portion that is engagable with the distal end of the inner member, and wherein the distal end comprises a rounded portion for facilitating the placement of the tissue on the inner leaves.

* * * * *